United States Patent [19]
De-Eknamkul et al.

[11] Patent Number: 5,879,916
[45] Date of Patent: Mar. 9, 1999

[54] GERANYLGERANIOL-18-HYDROXYLASE FROM *CROTON SUBLYRATUS*

[75] Inventors: Wanchai De-Eknamkul, Bangkok; Pimpimon Tansakul, Songkhla, both of Thailand

[73] Assignee: The Thailand Research Fund, Bangkok, Thailand

[21] Appl. No.: 923,789

[22] Filed: Sep. 4, 1997

Related U.S. Application Data

[60] Provisional application No. 60/054,454 Aug. 5, 1997.

[51] Int. Cl.$^6$ .............................. C12P 7/02; C12P 7/04; C12N 9/02
[52] U.S. Cl. ........................... 435/155; 435/157; 435/189
[58] Field of Search .................................... 435/155, 157, 435/189

[56] References Cited

U.S. PATENT DOCUMENTS

| | | | |
|---|---|---|---|
| 4,668,820 | 5/1987 | Ibata et al. | 560/248 |
| 5,264,638 | 11/1993 | Nilubol | 568/875 |

OTHER PUBLICATIONS

Tansakul et al. (1998) Phytochem., 47(7), "Geranylgeraniol–18–Hydroxylase: The Last Enzyme on the Plaunotol Biosynthetic Pathway in *Croton sublyratus*", pp. 1241–1246.

Anonymous, Drugs of Today, vol. 23 (1987), pp. 449–450.

Taniguchi, H., et al., "Role of the Electron Transfer System in Microsomal Drug Monooxygenase Reaction Catalyzed by Cytochrome P–450." *Archives of Biochemistry and Biophysics*, vol. 232, No. 2 (Aug. 1, 1984), pp. 585–596.

Loomis, D., et al., "Biochemistry of Terpenoids." in: Conn, E.E., *The Biochemistry of Plants* (New York, Academic Press 1981), pp. 364–411.

Madyashtha, K.M., et al., "Characterization of a Cytochrome P–450 Dependent Monoterpene Hydroxylase from the Higher Plant *Vinca rosea*." *Biochemistry*, vol. 15, No. 5 (1976), pp. 1097–1102.

Karp, F., et al., "Monoterpene Biosythesis: Specificity of the Hydroxylations of (—)–Limonene by Enzyme Preparations from Peppermint (*Mentha piperita*), Spearmint (*Mentha spicata*), and Perilla (*Perilla frutescens*) Leaves." *Archives of Biochemistry and Biophysics*, vol. 276, No. 1 (Jan., 1990), pp. 219–226.

Hallahan, D.L., et al., "Interactions of Avocado (*Persea americana*) Cytochrome P-450 with Monoterpenoids." *Plant Physiology*, vol. 98, (1992), pp. 1290–1297.

Morimoto, H., et al., "The effect of gelling agents on plaunotol accumulation in callus cultures of *Croton sublyratus* Kurz." *Plant Cell Reports*, vol. 8 (1989), pp. 210–213.

Kitazawa, E., et al., "New Esters of a Diterpene Alcohol from *Croton sublyratus*." *Annual Report of Sankyo Research Laboratories*, vol. 34 (1982), pp. 39–41.

Kitaoka, M., et al., "Accumulation of Geranylgeraniol in Cell Suspension Culture of *Croton sublyratus* Kurz (Euphorbiaceae)." *Annual Report of Sankyo Research Laboratories*, vol. 41 (1989), pp. 169–173.

Ogiso, A., et al., "Isolation and Structure of Antipeptic Ulcer Diterpene from Thai Medicinal Plant." *Chem. Pharm. Bulletin*, vol. 26, No. 10 (1978), pp. 3117–3123.

Ogiso, A., et al., "Original Plant of a Thai Crude Drug, Plau–noi." *Shoyakugaku Zasshi*, vol. 35, No. 1 (1981), pp. 287–290.

Ogiso, A., et al., "Plaunotol (CS–684), A New Anti–ulcer Agent." *Annual Report of Sankyo Research Laboratories*, vol. 37 (1985), pp. 1–39.

Kitazawa, E., et al., "Two Diterpene Alchohols from *Croton sublyratus*." *Phytochemistry*, vol. 20 (1981), pp. 287–289.

Chemical Abstracts, vol. 116, 1992, Abstract No. 116:170523d. Brit. UK Patent Application GB 2,246,128 "Extraction and purification of plaunotol from *Croton sublyratus*."

*Primary Examiner*—Jon P. Weber
*Attorney, Agent, or Firm*—Kremblas, Foster, Millard & Pollick

[57] ABSTRACT

Geranylgeraniol-18-hydroxylase, which catalyzes the C-18 hydroxylation of geranylgeraniol to form plaunotol, is extracted from *Croton sublyratus* using an extraction buffer and is purified using a differential centrifugation separation technique. The purified enzyme is used to convert geranylgeraniol to plaunotol, an anti-peptic ulcer agent. The enzymatic activity of the hydroxylase can be increased by a factor of about three by heating the enzyme in boiling water for about 30 minutes. The enzyme activity is also increased by adding a coenzyme, NADPH, which increases enzyme activity by a factor of about 2 or NADH, which increases activity by a factor of about 1.4. The pH optimum for hydroxylase enzyme activity is 5.0 The hydroxylase is a complex enzyme with a diameter of about 20 to 40 nm.

32 Claims, 5 Drawing Sheets

Geranylgeranyl diphosphate

↓ Phosphatase

Geranylgeraniol

↓ Geranylgeraniol 18-hydoxylase

Plaunotol

GERANYLGERANIOL-18-HYDROXYLASE FROM *CROTON SUBLYRATUS*

CROSS REFERENCE TO RELATED APPLICATION

This application claims the benefit of U.S. provisional application Ser. No. 60/054,454 filed on Aug. 5, 1997 all of which are incorporated by reference as if completely written herein.

BACKGROUND OF THE INVENTION

1. Technical Field of the Invention

This invention relates to a process for extracting and purifying an enzyme that is useful in the preparation of an anti-peptic ulcer drug. More specifically it relates to the enzyme geranylgeraniol-18-hydroxylase, a method for its extraction from plant parts using an extraction buffer, its purification using differential centrifugation, its heat activation, and its use in the production of plaunotol, a known anti-ulcer medication.

2. Background Description

Plaunotol, the active ingredient of a commercial drug named Kelnac® is a mucosal protective factor-enhancing anti-ulcer agent. It was originally found in the leaves of *Croton sublyratus* Kurz (Euphorbiaceae), a tropical plant found throughout southeast Asia. Although the structure of plaunotol has been known for almost twenty years, very little is known about its biosynthetic pathway. Although attempts have been made to establish *C. sublyratus* callus and cell cultures that yield high plaunotol content, none have been successful. A synthetic route to the production of plaunotol is known; however, the main source of plaunotol remains the extraction and purification from tropical plants as described, for example, in U.S. Pat. No. 5,264,638, all of which is incorporated herein by reference as if completely written herein. A less cumbersome and more effective process for the production of plaunotol is clearly needed.

SUMMARY OF THE INVENTION

It is an object of the present invention to provide a new process for the production of plaunotol. It is a further object of this invention to provide a purified enzyme that is useful in the synthesis of plaunotol. It is yet another object of this invention to provide a method of extracting this enzyme. It is an object of this invention to provide a heat activated enzyme. And it is still another object of this invention to provide an enzymatic process for the formation of plaunotol.

Accordingly, the present invention relates to a process for the extraction and purification of an geranylgeraniol-18-hydroxylase enzyme which is specific for the hydroxylation of geranylgeraniol at carbon 18 to afford plaunotol. The process consists of a) extracting *Croton sublyratus* plant parts such as leaves with an extraction buffer to obtain an extract of the geranylgeraniol-18-hydroxylase enzyme which is then purified by differential centrifugation.

The purified hydroxylase enzyme has hydroxylase activity at a pH of about 3 to about 10 with an optimal activity at a pH of about 5. The enzyme is specific for the hydroxylation of geranylgeraniol at carbon position 18 position to afford plaunotol. The enzyme exhibits an enhanced activity in the presence of a coenzyme and after heating, preferably at about 100° C. for about 30 minutes. The enzyme has a particle diameter of about 20 to about 40 nm.

A process for the production of plaunotol consists of hydroxylating the carbon 18 position of geranylgeraniol in the presence of purified geranylgeraniol-18-hydroxylase enzyme. The process is enhanced by carrying it out in the presence of a coenzyme, especially a coenzyme such as reduced nicotinamide adenine dinucleotide phosphate. The process is further enhanced by heating the enzyme at about 100° C. for about 30 minutes prior to is use in the hydroxylation process.

The foregoing and other features and advantages of the invention will become apparent from the following disclosure in which one or more preferred embodiments of the invention are described in detail and illustrated in the accompanying drawings. It is contemplated that variations in procedures and methods may appear to a person skilled in the art without departing from the scope of or sacrificing any of the advantages of the invention.

BRIEF DESCRIPTION OF THE DRAWINGS

FIG. 1 is a set of thin layer chromatography (TLC) radiochromatograms of reaction mixtures containing $[1-^3H]$ geranylgeranyl diphosphate (GGPP). Radioactivity in counts (cts) is shown on the vertical axes while the chromatogram position (distance) in cm is shown on the horizontal axes.

In describing the preferred embodiment of the invention which is illustrated in the drawings, specific terminology is resorted to for the sake of clarity. However, it is not intended that the invention be limited to the specific terms so selected and it is to be understood that each specific term includes all technical equivalents that operate in a similar manner to accomplish a similar purpose.

Although a preferred embodiment of the invention has been herein described, it is understood that various changes and modifications in the illustrated and described methods can be affected without departure from the basic principles that underlie the invention. Changes and modifications of this type are therefore deemed to be circumscribed by the spirit and scope of the invention, except as the same may be necessarily modified by the appended claims or reasonable equivalents thereof.

DETAILED DESCRIPTION OF THE INVENTION AND BEST MODE FOR CARRYING OUT THE PREFERRED EMBODIMENT

The present invention provides a process for extracting and purifying a hydroxylase enzyme by the general steps of extracting the enzyme from the plant *Croton sublyratus* to afford an extract and then purifying the extract by differential centrifugation. More specifically the extract is obtained from the *Croton sublyratus* plant by grinding the plant parts such as leaves into a fine powder. This can be accomplished by quick freezing fresh plant parts such as the leaves using liquid nitrogen and then grinding them in a pre-cooled mortar. The resulting fine powder is combined with an extraction buffer and allowed to thaw after which the resulting mixture is stirred at a sufficiently low temperature to avoid the action of various enzymes such as proteolytic enzymes in the crude extract. Typically a temperature range of about 0° to about 10° C. is used with a temperature of about 4° C. being preferred. Stirring is carried out for a sufficient time to effect enzyme solubilization, typically for about twenty minutes.

Various buffers can be used for the extraction provided that the buffer can efficiently solubilize the enzyme. Generally, buffers with a pH in the range of about 3 to about 9 can be used, but it is to be realized that a pH above about 8 tends to promote air oxidation while a pH below about 6 may increase undesirable protease activity. Preferably a buffer in the pH range of about 6 to about 8 which can efficiently solubilize the enzyme is used for the extraction. For example, an 83 mM buffer of N-tris(hydroxymethyl) methylglycine (tricine) and sodium hydroxide at a pH of about 7.8 provides good results.

The ionic strength of the buffer facilitates precipitation of the microsomal membrane during centrifugation. The ionic strength of the buffer is not critical.

Magnesium chloride ($MgCl_2$) typically is used for ionic strength adjustment and can range from about 5 mM to about 50 mM with a preferred range of about 7.5 mM to about 20 mM and a most preferred concentration of about 10 mM being used.

One or more thiol protectants are used to maintain the thiol groups thought to be present in the hydroxylase enzyme. Such thiol protectants include β-mercaptoethanol and 1,4-dithio-dl-threitol (DTT). The β-mercaptoethanol is used as a general reducing agent while the DTT acts to keep sufhydryl groups in their reduced form and may inhibit polyphenol oxidase enzymes. The β-mercaptoethanol may be used in a concentration range of about 0.001 mM to about 50 mM with a range of about 0.5 mM to about 10 mM being preferred and a concentration of about 1.0 mM most preferred. The DTT may be used in a concentration range of about 0.01 mM to about 30 mM with a range of about 0.5 mM to about 10 mM being preferred and a concentration of about 5.0 mM most preferred.

Bovine serum albumin (BSA) and a polyhydric alcohol such as glyerol or a sugar such as sucrose were added to the buffer as enzyme stabilizers. BSA stabilizes the enzyme by acting as a substrate for various endogenous proteolytic enzymes in the crude extract and thereby prevents the enzyme from enzymatic degradation. The polyhydric alcohol stabilizes the enzyme at low protein concentration by maintaining the tertiary structure of the enzyme in the cell-free system. Although various concentrations of BSA (about 0.05 to about 1.0% (weight/volume (w/v)) of extraction buffer) and sucrose (about 0.1M to about 0.5M) can be used, the presence of high BSA (about 1% w/v) and sucrose (about 0.4M) concentrations in the extraction buffer are preferred.

Ethylenediaminetetraacetic acid (EDTA) was used as a protease inhibitor, particularly to inhibit the enzyme class of metalloproteases. EDTA also chelates heavy metal ions that could affect the protein and promote oxidation. The concentration range of EDTA is about 0.1 mM to about 20 mM with the preferred range about 1.0 mM to about 15 mM and the most preferred range about 10 mM.

The suspension resulting from the stirring of powdered leaves and extractant buffer was filtered by pressing the suspension through four layers of cheese cloth. Alternatively filtration of the suspension through Miracloth® using suction filtration with a Buchner funnel and a suction flask may also be possible. However, care must be taken to avoid foam formation which could deactivate the target enzyme.

The resulting filtrate was centrifuged at about 3,000 g for about ten minutes. The resultant supernatant was further centrifuged at about 20,000 g for about twenty minutes. The resulting 20,000 pellet contained the purified hydroxylase enzyme and was resuspended in a buffer of 100 mM tricine-NaOH at a pH of about 7.8 that contained about 5 mM β-mercaptoethanol, about 1 mM of DTT, about 0.2M sucrose, about 1 mM EDTA and 15% glycerol. The components and their concentrations in this buffer were slightly modified from those used in the extraction buffer. One reason for the modification was to place the 20,000 g microsomal fraction in condition for further processing. Addition of 15% volume/volume (v/v) glycerol to the buffer facilitates microsomal storage at −20° C. without significant effect on the enzyme activity during freezing and thawing. The sucrose concentration was reduced by about 50% (from 0.4M to about 0.2M) since there is no longer any leaf water (approximately 80%) to dilute the sucrose concentration as was the case with the extraction buffer. Although glycerol and sucrose appear to have similar effects in enzyme stabilization, the presence of glycerol (about 5 to about 15% v/v) seemed to provide additional stabilization during enzyme storage. The tricine buffer concentration was increased slightly to about 100 mM to increase the buffer capacity during enzyme storage.

The resuspended microsomal fraction was heated for up to about forty-five minutes and preferably for about ten to about 35 minutes and most preferably for about thirty minutes in boiling water, that is, at about 100° C. to further activate the enzyme.

EXPERIMENTAL

Chemicals. Plaunotol was obtained from Kelnac® soft gelatin capsules which were manufactured by Sankyo Co., Ltd, Tokyo, Japan; [1-$^3$H] Geranylgeranyl diphosphate, triammonium salt (specific activity=19.3 Ci/mmol, 0.5 mCi/ml) was purchased from Du Pont de Nemours (Wilmington, Del.), geranylgeraniol (GGOH), farnesol, geraniol, reduced nicotinamide adenine dinucleotide phosphate (NADPH), reduced nicotinamide adenine dinucleotide (NADH) and 1,4 dithio-dl-threitol (DTT) were purchased from Sigma Chemical Company, St. Louis, Mo.

Plant materials. The leaves of *C. sublyratus* were obtained from plants growing in the open field at the Faculty of Pharmaceutical Sciences, Chulalongkorn University, Bangkok, Thailand.

Preparation of the microsomal enzyme. Fresh leaves (30 g) of *C. sublyratus* were quick frozen using liquid nitrogen and ground in a pre-cooled mortar. The resulting fine powder was mixed with 60 ml of an extraction buffer and allowed to thaw and then stirred for 20 min at 4° C. The extraction buffer consisted of 83 mM tricine-NaOH at a pH of 7.8 and contained 5 mM β-mercaptoethanol, 0.4M sucrose, 10 mM EDTA, 1 mM DTT, 10 mM $MgCl_2$ and 1.0% (w/v) BSA. The resulting suspension was pressed through four layers of cheese-cloth and the filtrate was centrifuged at 3,000 g for 10 min. The 3,000 g supernatant was further centrifuged at 20,000 g for another 20 min. The resulting 20,000 g pellet was resuspended in 10 ml of 0.1M tricine-NaOH (pH 7.8), containing 5 mM β-mercaptoethanol, 1 mM DTT, 0.2M sucrose, 1 mM EDTA and 15% glycerol. To heat activate the enzyme preparation, the resuspended 20,000 g microsomal fraction was heated in boiling water for about 30 min before being used.

Detection of enzymatic products of $[1-^3H]$ geranylgeranyl diphosphate (GGPP). The enzyme activities of the microsomal fraction which are responsible for the catalysis in plaunotol biosynthesis were examined in a reaction mixture containing 0.045 nM $[1-^3H]$ geranylgeranyl diphosphate (GGPP), 0.13 $\mu$Ci (microcuries); 83 mM tricine, pH (7.8), 0.8 mM NADPH and 100 $\mu$l of enzyme solution in a total volume of 150 $\mu$l. The reaction mixture was incubated at 30° C. for 30 min and for other time intervals. The reaction was terminated by diethylether extraction and then subjected to thin-layer chromatography (TLC; silica gel 60 F254) using a solvent system of chloroform:n-propanol in a (24:1) volume ratio. The TLC plate was then scanned with a TLC-radioscanner to produce radiochromatograms.

Enzyme Assay. The enzyme activity of GGOH-18-hydroxylase was determined by using TLC densitometry. The microsomal enzyme was incubated at 30° C. in a reaction mixture containing 1 mM GGOH, 0.8 mM NADPH, 83 mM tricine buffer at a pH of 7.8 and 100 $\mu$l of the microsomal fraction in a total volume 300 $\mu$l. After about 30 min of incubation, the reaction mixture was extracted with diethylether and chromotographed on a TLC plate (silica gel G 60 F254) using chloroform:n-propanol mixture in a 24:1 volume ratio with triple development. The resulting TLC plate chromotograms were then scanned with a TLC densitometer ($\lambda_{max}$=210 nm). The amount of the enzymatic product formed was estimated from the area under the peak of plaunotol ($R_f$=0.46) and the calibration curve of a plaunotol standard which showed a linear relationship between 0.5 to 15 nmol of plaunotol. The regression analysis gave a correlation coefficient of 0.996994 with a linear slope of 1.928. The following buffers were used to obtain the optimal pH of the enzyme: a 0.1M sodium acetate buffer for a pH of 4, 4.5 and 5.0; a 0.1M sodium phosphate buffer for a pH of 6.5; a 0.1M tricine buffer for a pH of 7.0, 7.8 and 8.0; and a 0.1M glycine buffer for a pH of 9.0, and 10.0.

Product Identification. The hydroxylation product was identified by direct comparisons with a known plaunotol sample by gas chromatography (GC), chemical ionization mass spectrometry (CI-MS), and infrared spectroscopy (IR). The GC capillary column was a DB-5 (30×0.25 mm) column with a detector and injector temperature of 250° C. Initially the column was held at temperature 150° C. holding for 3 minutes and then heated at a 10° C./min until a temperature of 300° C. was reached which temperature was then held for 20 min. Methane was used as the reagent gas in the chemical ionization mass spectrometer (CI-MS). The IR spectra ere taken by dissolving the enzymatic product or a known sample of plaunotol in chloroform. The solution was placed in a KBr liquid cell and the solvent was evaporated before the spectra were taken.

Electron micrographs. A heated microsomal fraction that had been heated or 30 min at about 100° C. was centrifuged at 20,000 g for 20 min. The supernatant liquid exhibited 18-hydroxylase activity and was concentrated with a Centricon-10 concentrator. The concentrated, heat-activated enzyme then was examined with a transmission electron microscope and electron micrographs obtained.

Figure 1A:
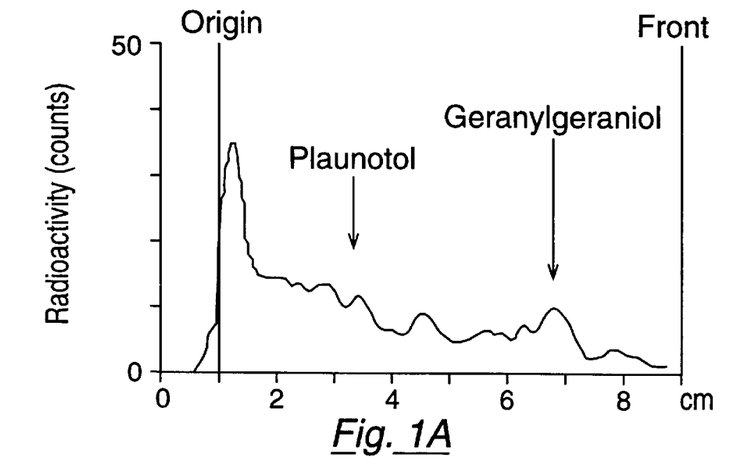
FIG. 1A is a chromatogram of the product found in the 3,000 g centrifugation pellet.
Figure 1B:
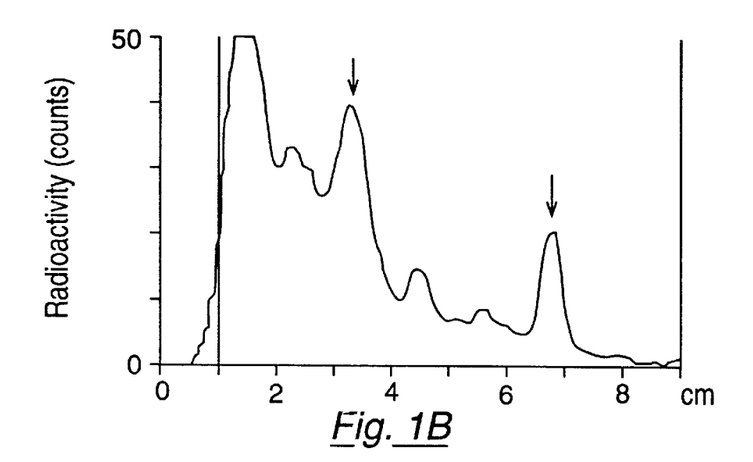
FIG. 1B is a chromatogram of the product found in the 20,000 g centrifugation pellet.
Figure 1C:
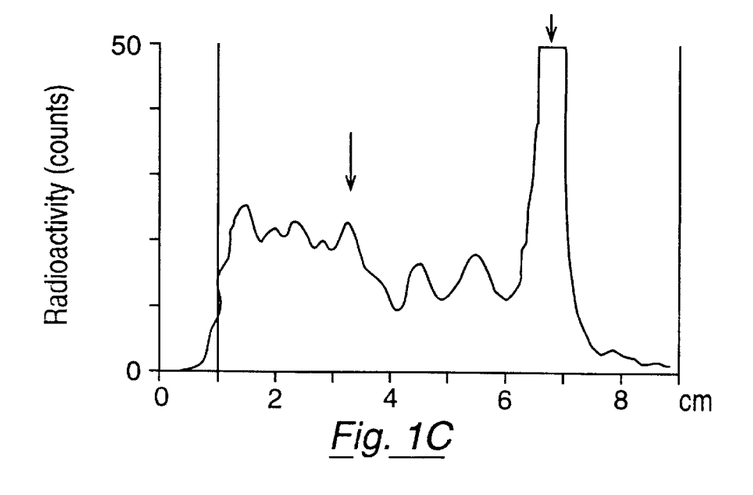
FIG. 1C is a chromatogram of the product found in the 20,000 g centrifugation supernatant liquid.

Geranylgeraniol-18-hydroxylase activity. The enzyme activity of geranylgeraniol-18-hydroxylase was examined in different centrifugation fractions of a crude enzyme extract prepared from *C. sublyratus* leaves. Radioactively labelled $[1-^3H]$ geranylgeranyl diphosphate (GGPP) was used as a substrate and the enzymatic reaction products were determined using a TLC-radioscan. As seen in FIG. 1A, the TLC-radiochromatogram of the 3,000 g pellet showed very low radioactivity at the geranylgeraniol (GGOH) and the plaunotol positions. The chromatogram of the 20,000 g microsomal fraction, on the other hand, clearly showed the radioactive peaks of both compounds (FIG. 1B). For the 20,000 g supernatant fraction, only the GGOH peak was detected (FIG. 1C). This shows that phosphatase activities were present in both 20,000 g and 20,000 g supernatant fractions whereas the activity of GGOH-18-hydroxylase was present primarily in the 20,000 g microsomal (pellet) fraction.

Figure 2:
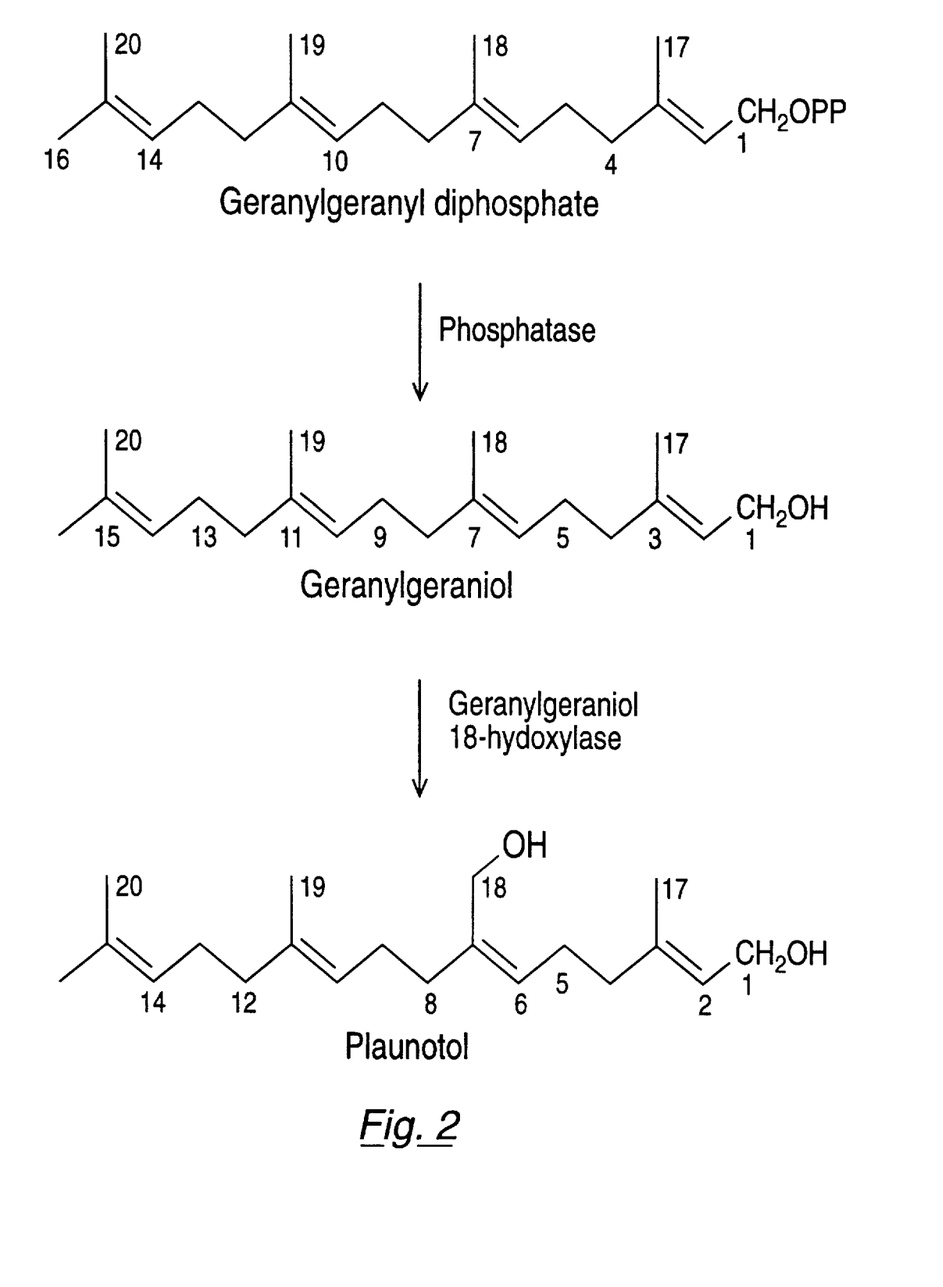
FIG. 2 illustrates the formation of plaunotol from geranylgeranyl diphosphate along with the structure and indication of carbon numbering in each material.
Figure 3:
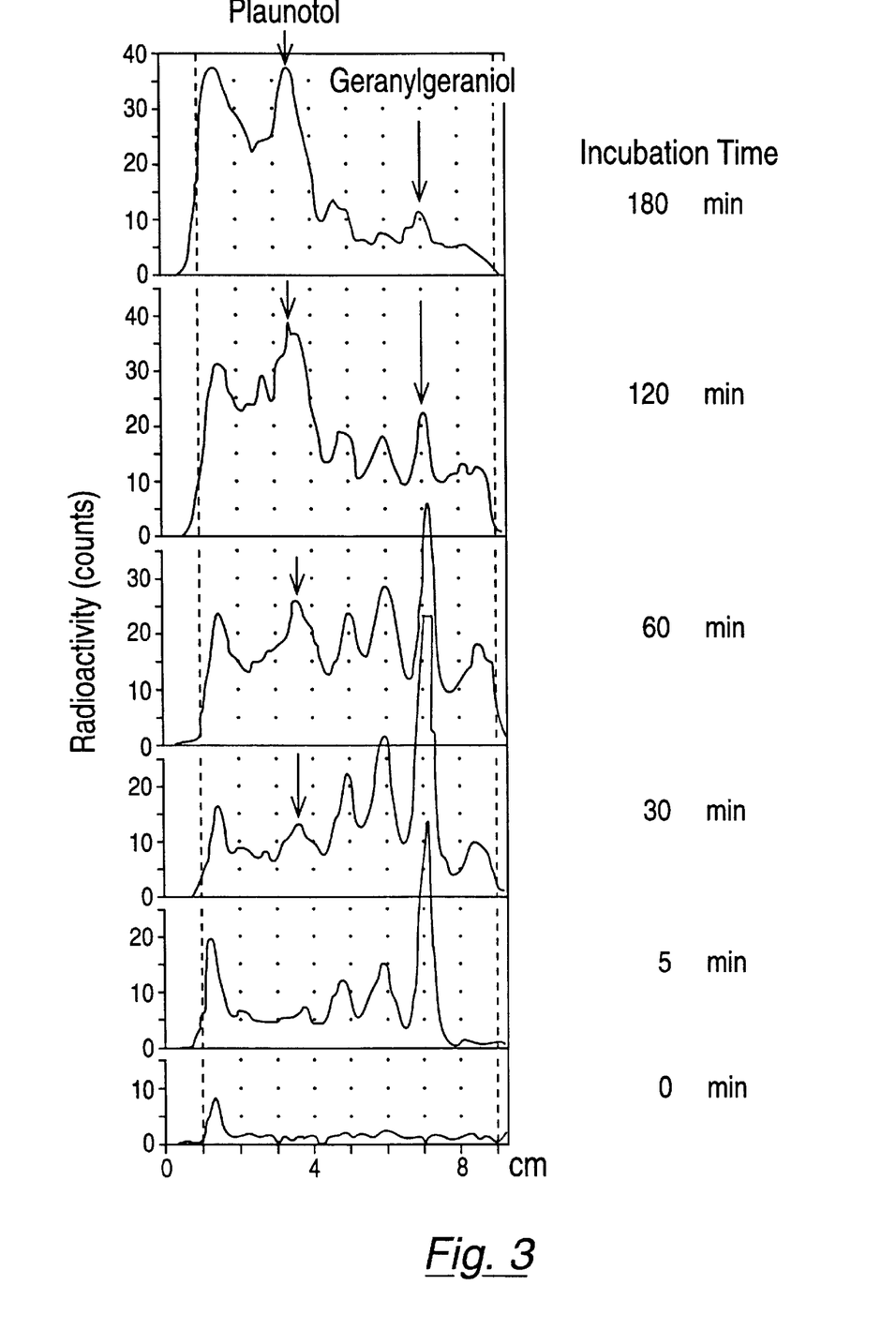
FIG. 3 is a set of TLC radiochromatograms from a time study of the conversion of GGPP to geranylgeraniol (GGOH) and plaunotol by the 20,000 g centrifugation pellet (microsomal) fraction of an extract of *Croton sublyratus* leaves. The chromatograms from bottom to top were taken at 0, 5, 30, 60, 120, and 180 minutes. Radioactivity in counts (cts) is shown on the vertical axes while the chromatogram position (distance) in cm is shown on the horizontal axes.

To confirm the biosynthetic formation of plaunotol from GGPP (FIG. 2), a time-study of the conversion of $[1-^3H]$ GGPP by the microsomal fraction was undertaken. An aliquot of the incubation mixture was taken at 5, 30, 60, 120 and 180 min and the radioactive product formation detected. As shown in FIG. 3, $[1-^3H]$ GGPP was rapidly converted within 5 min to the major GGOH peak and a few minor peaks with lower $R_f$ values. The peak of GGOH increased to a maximum in 30 minutes followed by a continuous decrease of the peak until it almost disappeared at 180 min. Simultaneously, the plaunotol radioactive peak showed a continuous increase during the entire time-study. These results demonstrate that the GGPP in the incubation mixture was first hydrolyzed by the phosphatase enzyme to form GGOH followed by C-18 hydroxylation of GGOH catalyzed by GGOH-18-hydroxylase to form plaunotol and, thus, confirmed the proposed plaunotol biosynthetic pathway shown in FIG. 2.

Figure 4:
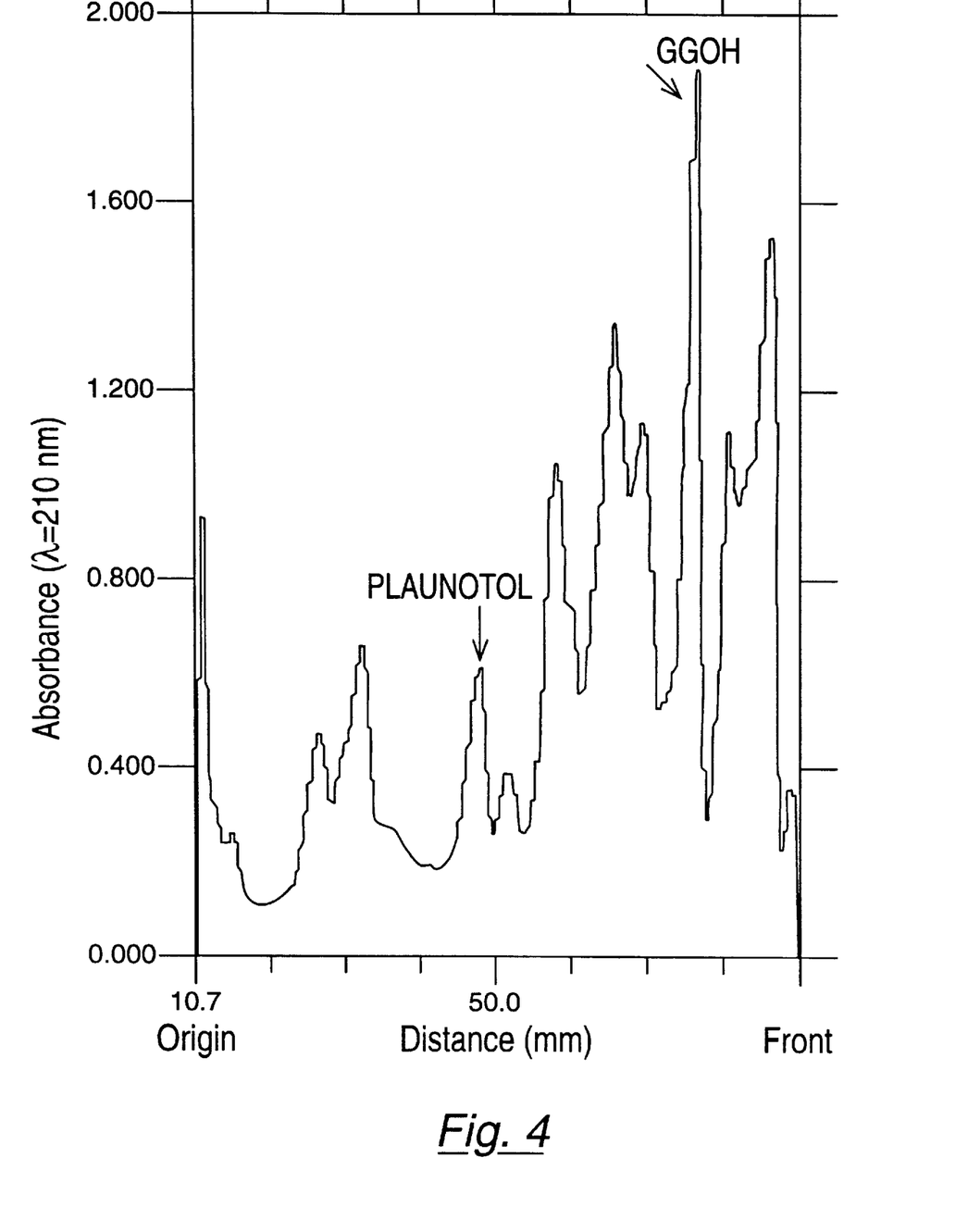
FIG. 4 is a typical chromatogram of a reaction mixture of GGOH and the 20,000 g microsomal (pellet) fraction containing active geranylgeraniol-18-hydroxylase (GGOH-18-hydroxylase) separated by TLC and scanned with a TLC scanner at $\lambda=210$ nm. The $R_f$ values of plaunotol and GGOH are 0.46 and 0.81, respectively. Absorbance ($\lambda=210$ nm) is given on the vertical axis while distance in mm is given on the horizontal axis.

Development of enzyme assay. An enzyme assay based on a TLC-densitometry technique was developed to determine the catalytic activity of GGOH-18-hydroxylase. For this technique, non-radioactively labelled GGOH was used as the substrate and the reaction was terminated by extraction with diethylether. Both the substrate and the plaunotol reaction product were extracted into the ether phase but subsequently separated by TLC followed by densitometric scanning of the plate at $\lambda_{210}$ nm to produce the chromatogram. FIG. 4 shows a typical TLC-chromatogram of a reaction mixture containing the 20,000 g microsomal fraction with active GGOH-18-hydroxylase. A clear separation of plaunotol from the other compounds is shown. The GGOH substrate appeared at $R_f$ 0.81 whereas the plaunotol product was at 0.46. The enzyme activity of GGOH-18-hydroxylase was determined on the basis of the area under the plaunotol peak and its standard curve which showed linearity between 0.5 and 15 nmol plaunotol, that is, hydroxylase activity was constant over time and increased with increasing enzyme concentration.

Product identification. The enzyme assay was used to show that plaunotol formation is an enzymatic reaction that increases with time and with increasing amounts of microsomal protein. In order to identify the enzymatic reaction product, a large-scale (250-fold) incubation of the microsomal fraction with GGOH was carried out. The resulting incubation mixture was worked up by ether extraction and preparative TLC purification to obtain the reaction product. The product was then identified by direct comparison with authentic plaunotol by both GC-MS and IR. For GC, the retention time of the enzymatic product (9.25 min) was very close to that of the plaunotol standard (9.31 min). Analysis of both peaks by CIMS showed identical mass spectra with $[(M+1)^+-H_2O]$ at 289 and $[(M+1)^+-2H_2O]$ at 271. For IR spectra, both the product and plaunotol showed characteristic absorption $vCHCl_3 cm^{-1}$: 3350, 2923, 1645, 1379 and 1016. These results confirmed that the enzymatic product was plaunotol and the enzyme catalyzing the reaction was GGOH-18-hydroxylase.

PROPERTIES OF GERANYLGERANIOL- 18-HYDROXYLASE

Figure 5:
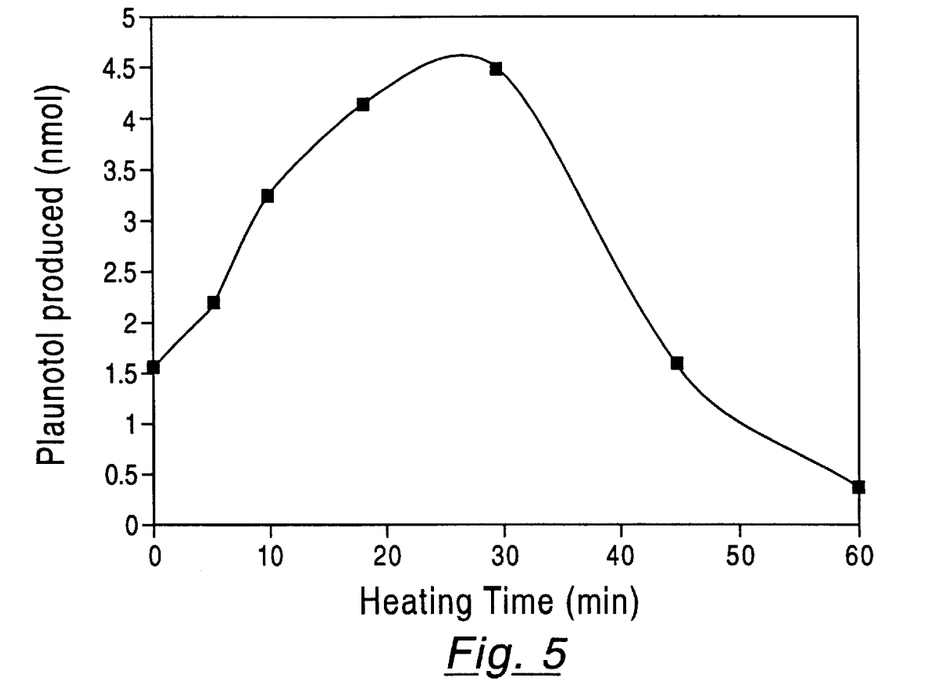
FIG. 5 is a graph of the amount of plaunotol produced in nmol (vertical axis) versus the heating time in min of the GGOH-18-hydroxylase from the 20,000 g pellet at 100° C. prior to the reaction with GGOH (horizontal axis).

Effect of heating on enzyme activity. During the course of this study, it was noted that the boiled control sample frequently showed higher enzyme activity than the experimental sample. To explore this further, the microsomal fraction was heated at 100° C. for 5, 10, 20, 30, 45 and 60 min before being put into the reaction mixture. Each mixture was incubated for 30 min at 30° C. and analyzed for plaunotol using the enzyme assay described previously. Geranylgeraniol-18-hydroxylase (GGOH-18-hydroxylase) activity was found to increase over the first 30 min of the 20,000 g microsomal fraction pellet) heating (FIG. 5). Thereafter, the enzyme activity declined rapidly and was almost non-detectable after 60 min of boiling. These results clearly show the positive effect of microsomal heating (30 min) on enhancing enzyme activity.

Figure 6:
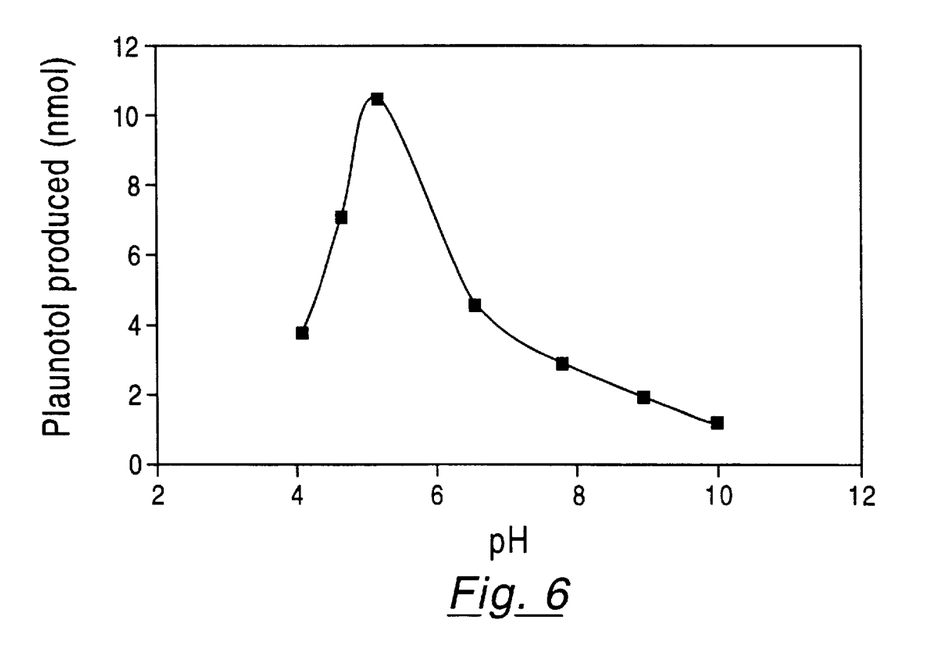
FIG. 6 is a graph of the amount of plaunotol produced in nmol (vertical axis) versus the pH of the GGOH-18-hydroxylase and GGOH reaction mixture (horizontal axis).

The enzyme activity increased about 3-fold when the microsomal fraction was heated for about 30 min prior to being put into the reaction mixture. This increase could be due to the presence of heat-labile enzyme inhibitors that are present in the microsomal fraction and that are destroyed on boiling while the complex hydroxylase enzyme remains active.

pH. The typical pH used in the incubation process was 7.8. However, studies of the effect of pH on enzyme activity have shown that the pH optimum of the enzyme is at about 5.0. Above or below this pH value, the enzyme activity decreases rapidly (FIG. 6). It is noted that the optimal value of 5.0 is relatively low as compared with other cytochrome P-450 related monoterpenoid hydroxylases.

Coenzymes. The hydroxylation activity of the microsomal fraction was found to depend on a coenzyme such as NADPH which was the best electron donor tested. When NADH was substituted for NADPH, the activity was about 70% of NADPH. However, the hydroxylation of GGOH by the microsomal fraction was also detected in the absence of these co-factors with an activity of about 54% of NADPH.

Substrate specificity. The substrate specificity of GGOH-18-hydroxylase of a heat activated microsomal fraction was also investigated. The substrates chosen for the comparison included the terpenes, GGOH, farnesol and geraniol. Among these, only GGOH hydroxylation was promoted by the enzyme. Neither the sesquiterpenoid, farnesol, nor the monoterpenoid, geraniol, was converted to its hydroxy derivative by the microsomal fraction.

Electron micrographs or the heated microsomes. The physical dimensions of the microsomal fraction that contain the GGOH-18-hydroxylase activity were observed with an electron microscope. The 20,000 g microsomal fraction was first heated for 30 min and the fraction was then centrifuged at 20,000 g for 20 min to separate the supernatant and pellet. Detection of the enzyme activity in each fraction showed that most of the activity was present in the supernatant (Table I). The supernatant was concentrated using Centriton-10 concentrator before being used for specimen preparation for negative staining, electron microscope observation. The resulting electron micrographs revealed the presence of particles with diameters ranging from 20 to 40 nm which indicates that the hydroxylase is a complex enzyme.

TABLE I

Enzyme Activity and Protein Content

| Sample | Total enzyme activity (nmole/30 min/ml) | Total protein (mg/ml) |
|---|---|---|
| Heated microsomal enzyme | 49.4 | 0.34 |
| 20,000 g pellet from heated microsomal enzyme | 7.6 | 0.23 |
| Supernatant from heated microsomal enzyme | 28.9 | 0.19 |

Uses. The geranylgeraniol-18-hydroxylase enzyme is especially useful for the biotransformation of geranylgeraniol to plaunotol. The hydroxylase enzyme is extracted from the *Croton sublyratus* plant and purified according to the process noted above. The enzyme is then heat treated to about 100° C. for about one-half hour to increase the enzyme activity by a factor of about three. Both purification and heat treating remove undesirable materials in the plant extract that would otherwise result in unwanted side reactions in the GGOH bioconversion. The purified and heat-treated enzyme is mixed with the GGOH in a suitable buffer to maintain a reaction mixture pH of about 4 to 7 with a pH of about 4.5 to 5.5 preferred and a pH of about 5.0 most preferred. Any suitable buffering system may be used such as a sodium acetate buffer. A coenzyme such as NADPH or NADH may be used. NADPH is preferred because of its superior activation ability. Other reagents added to the reaction mixture can include β-mercaptoethanol or DTT or both as thiol protectants and polyhydric alcohols such as sucrose or glycerol or both as enzyme stabilizers. The resultant mixture is incubated at about 30° C. with mixing until the reaction is complete. The resulting plaunotol is recovered by solvent extraction and chromatographic purification.

Alternatively the purified and heat activated enzyme is immobilized on a suitable support such as Sephadex, Bio-Gel, Porasil, etc. and packed into a column. A suitable reaction mixture containing the GGOH substrate is then circulated through the column to convert it to plaunotol which is then isolated and purified using conventional techniques.

It is possible that changes in configurations to other than those shown could be used but that which is shown if preferred and typical. Without departing from the spirit of this invention, various means of fastening the components together may be used.

It is therefore understood that although the present invention has been specifically disclosed with the preferred embodiment and examples, modifications to the design concerning sizing and shape will be apparent to those skilled in the art and such modifications and variations are considered to be equivalent to and within the scope of the disclosed invention and the appended claims.

We claim:

1. A process for the extraction and purification of an geranylgeraniol-18-hydroxylase enzyme specific for the hydroxylation of geranylgeraniol at carbon 18 to afford plaunotol, said process comprising:
   a) extracting a *Croton sublyratus* plant with an extraction buffer to obtain an extract of said geranylgeraniol-18-hydroxylase enzyme; and
   b) purifying said geranylgeraniol-18-hydroxylase from said extract by differential centrifugation to recover said purified geranylgeraniol-18-hydroxylase enzyme.

2. The process according to claim 1 further comprising the step of activating said geranylgeraniol-18-hydroxylase obtained from said purifying step by heating.

3. The process according to claim 2 wherein said activating step is carried out by heating at about 100° C.

4. The process according to claim 3 wherein said activating step is carried out by heating at about 100° C. for up to about thirty minutes.

5. The process according to claim 1 wherein leaves of said *Croton sublyratus* plant are extracted.

6. The process according to claim 1 further comprising steps of quick freezing said *Croton sublyratus* plant to afford a frozen plant and grinding said frozen plant to give a powder prior to said extraction step.

7. The process according to claim 6 further comprising a step of stirring said powder with said extraction buffer to afford a suspension.

8. The process according to claim 7 further comprising a step of filtering said suspension to afford said extract.

9. The process according to claim 1 wherein said purifying step is carried out by centrifuging said extract at about 3000 g to afford a supernatant liquid followed by a second centrifuging of said supernatant liquid at about 20,000 g to afford a pellet of said purified geranylgeraniol-18-hydroxylase.

10. The purified enzyme according to claim 9 wherein said heating is carried out at about 100° C. for about thirty minutes.

11. The process according to claim 1 with said extraction buffer comprising:
   a) at least one component for adjusting an ionic strength of said extraction buffer;
   b) at least one enzyme thio protectant;
   c) at least one enzyme stabilizer; and
   d) at least one component used as a protease inhibitor.

12. The process according to claim 11 wherein said at least one component for adjusting said ionic strength of said extraction buffer is magnesium chloride.

13. The process according to claim 11 wherein said at least one enzyme thio protectant is selected from the group consisting of 2-mercaptoethanol and 1,4 dithio-dl-threitol.

14. The process according to claim 11 wherein said at least one enzyme stabilizer is selected from the group consisting of a polyhydric alcohol and bovine serum albumin.

15. The process according to claim 14 wherein said polyhydric alcohol is selected from the group consisting of glycerol and sucrose.

16. The process according to claim 15 wherein said at least one protease inhibitor is ethylene diaminetetraacetic acid.

17. The process according to claim 1 wherein said extraction buffer comprises N-[tris(hydroxymethyl)methyl] glycine and sodium hydroxide.

18. The purified geranylgeraniol-18-hydroxylase enzyme obtained from the process of claim 1.

19. The purified enzyme according to claim 18 activated by heating.

20. A process for producing plaunotol comprising the step of reacting said purified enzyme formed according to claim 1 with geranylgeraniol.

21. The process according to claim 20 wherein said process is carried out at a pH of about three to about ten.

22. The process according to claim 21 wherein said process is carried out at a pH of about four to about seven.

23. The process according to claim 22 wherein said process is carried out at a pH of about five.

24. A process for the production of plaunotol comprising catalyzing the hydroxylation of the C-18 position of geranylgeraniol with the purified geranylgeraniol-18-hydroxylase enzyme according to claim 18 to form said plaunotol, and recovering said plaunotol.

25. The process according to claim 24 further comprising the step of heating said purified geranylgeraniol-18-hydroxylase enzyme prior to said hydroxylation step.

26. The process according to claim 25 wherein said heating step is carried out at a temperature of about 100° C. for about thirty minutes.

27. The process according to claim 24 wherein hydroxylation of said C-18 position of said geranylgeraniol catalyzed by geranylgeraniol-18-hydroxylase enzyme is carried out at a pH of about five.

28. The process according to claim 24 wherein hydroxylation of said C-18 position of said geranylgeraniol catalyzed by geranylgeraniol-18-hydroxylase enzyme is carried out in the presence of a coenzyme.

29. The process according to claim 28 wherein said coenzyme is reduced nicotinamide adenine dinucleotide phosphate.

30. A purified hydroxylase enzyme obtained from *Croton sublyratus* having hydroxylase activity in a pH range of about 3 to about 10 with an optimal activity at a pH of about 5, said enzyme being specific for the hydroxylation of geranylgeraniol at a carbon 18 position to afford plaunotol; said enzyme having enhanced activity in the presence of a coenzyme; and said enzyme having a particle diameter of about 20 nm to about 40 nm.

31. The purified enzyme according to claim 30 activated by heating.

32. The purified enzyme according to claim 30 activated by heating at 100° C. for about thirty minutes.

* * * * *